(12) United States Patent
Asma et al.

(10) Patent No.: US 8,507,869 B2
(45) Date of Patent: Aug. 13, 2013

(54) METHODS AND SYSTEMS FOR ADAPTIVE TOMOGRAPHIC IMAGING

(75) Inventors: Evren Asma, Niskayuna, NY (US); Ravindra Mohan Manjeshwar, Glenville, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 13/282,586

(22) Filed: Oct. 27, 2011

(65) Prior Publication Data
US 2013/0105699 A1 May 2, 2013

(51) Int. Cl.
*G01T 1/166* (2006.01)
(52) U.S. Cl.
USPC .................................................. 250/363.03
(58) Field of Classification Search
USPC .................................................. 250/363.03
See application file for complete search history.

(56) References Cited

U.S. PATENT DOCUMENTS

| | | | | |
|---|---|---|---|---|
| 7,439,514 | B1 * | 10/2008 | Uribe et al. | 250/363.1 |
| 7,569,826 | B2 * | 8/2009 | Uribe et al. | 250/363.01 |
| 7,723,690 | B2 * | 5/2010 | Uribe et al. | 250/363.1 |
| 7,813,783 | B2 | 10/2010 | Thomas et al. | |
| 7,928,727 | B2 | 4/2011 | Vija et al. | |
| 2007/0280519 | A1 * | 12/2007 | Spies et al. | 382/131 |
| 2009/0261256 | A1 | 10/2009 | Wieczorek | |
| 2010/0155608 | A1 | 6/2010 | Devito et al. | |
| 2010/0308228 | A1 | 12/2010 | Vija et al. | |

OTHER PUBLICATIONS

Barrett et al.,"Adaptive SPECT", IEEE Transactions on Medical Imaging,vol. 27, Issue 6, Jun. 2008; Abstract—1Page.
Masuda et al.,"Comparison of Imaging Protocols for 18F-FDG PET/CT in Overweight Patients: Optimizing Scan Duration Versus Administered Dose", The Journal of Nuclear Medicine, vol. 50, Issue 6, pp. 844-848, Jun. 2009.
Oshinski et al.,"Cardiovascular Magnetic Resonance at 3.0T: Current State of the Art", Journal of Cardiovascular Magnetic Resonance,vol. 12, Issue 1, pp. 55, 2010; 13 Pages.
Asma et al.,"Adaptive Acquisition Protocol Design for Local CNR Maximization in Flexible SPECT and PET Scanners",2010 IEEE Nuclear Science Symposium Conference Record (NSS/MIC), Oct. 30-Nov. 6, 2010; Abstract 2 Pages.
Asma et al.,"SPECT Acquisition Protocol Design for Local Performance Optimization", Journal of Nuclear Medicine, vol. 52, Issue 1, pp. 488,2011.
Nan Li et al.; "Adaptive Angular Sampling Approach for Emission Tomography"; 978-1-4244-9105-6/10 © 2010 IEEE; pp. 2903 7 Pages.
Kathleen Vunchx et al.; "Fisher Information-Based Evaluation of Image Quality for Time-of-Flight PET"; IEEE Transactions on Medical Imaging, vol. 29, No. 2, Feb. 2010; 11 Pages.
Jian Zhou et al.; "Adaptive Imaging for Lesion Detection Using a Zoom-in PET System"; IEEE Transactions on Medical Imaging, vol. 30, No. 1, Jan. 2011; 12Pages.

\* cited by examiner

*Primary Examiner* — Marcus Taningco
(74) *Attorney, Agent, or Firm* — Marie-Claire B. Claire

(57) ABSTRACT

Nuclear imaging systems, non-transitory computer readable media and methods for adaptive imaging are presented. Particularly, the present method includes acquiring preliminary projection data by scanning each of one or more views of a subject for a determined preliminary scan interval. Further, a region of interest of the subject is identified. The preliminary projection data is then used to perform a constrained optimization of a rapidly computable image quality metric for determining an acquisition protocol that improves the image quality metric at the identified region of interest. Particularly, the determined acquisition protocol is used to acquire target projection data corresponding to at least the identified region of interest. Further, an image of at least the identified region of interest is reconstructed using the target projection data, the preliminary projection data, or a combination thereof.

20 Claims, 5 Drawing Sheets

METHODS AND SYSTEMS FOR ADAPTIVE TOMOGRAPHIC IMAGING

BACKGROUND

Imaging systems often include fixed geometries that are used to scan objects of various dimensions and characteristics in a variety of different imaging scenarios. Such systems, however, may not be optimized for specific patients and imaging requirements, often resulting in decreased sensitivity and resolution. The decrease in sensitivity, in turn, translates into higher radiation dosage for a subject or sub-optimal imaging. Accordingly, currently available imaging systems sub-optimally distribute the exam scan time and/or employ prolonged scans to acquire adequate imaging statistics. Such exams, however, compromise patient comfort and often result in image artifacts caused by patient motion, in turn, leading to inaccurate diagnoses.

Recent advances in imaging system design aim to reduce scan intervals, or alternatively, the radiation dose administered to the patient by using new and improved components such as detectors and collimators. Certain imaging systems, for example, include custom detector geometry, innovative collimation designs including multiple pinhole or slit-hole collimators and use of solid-state detectors for improving diagnostic imaging processes. Particularly, adaptive imaging systems allow for autonomously altering data-acquisition configurations or protocols in near real time for improving image reconstruction.

Adaptive imaging, in particular, aims to optimize one or more of the system parameters in near real time for reducing radiation dose while simultaneously improving image quality over conventional implementations. A conventional single photon emission computed tomography (SPECT) system, for example, typically employs a uniform scan speed, which determines the time that a detector remains at a specific view angle for acquiring "counts" or gamma emission events. The acquired data, however, can vary significantly from one view to another owing to characteristics of the particular region of interest (ROI) being imaged, a view angle, attenuation and finite collimator resolution. Accordingly, the gamma radiation emanating from one particular view angle can have an effective count rate that is different from the effective count rate at another view angle. In a SPECT implementation using a uniform scan and a specified total scan interval, the time spent by the detector at each view angle, thus, may be longer or shorter than appropriate to gather sufficient projection data for generating the PET or SPECT image of a desired spatial resolution.

Accordingly, some present day systems are known to employ certain adaptive imaging techniques for improving diagnostic scanning. By way of example, recent research on adaptive imaging protocols entail use of derived expressions for the performances of ideal linear observers and linear estimators. Certain other techniques are drawn to adaptive zoom-in positron emission tomography (PET) systems with an insert placed into a PET scanner for imaging a small field of view in high resolution. Furthermore, most of the recent techniques for improving image quality metrics require 'a priori' knowledge of the lesion or tumor being imaged, which is typically determined from the reconstruction of scout data.

BRIEF DESCRIPTION

Certain aspects of the present technique are drawn to a method for adaptive imaging. Preliminary projection data is acquired by scanning each of one or more views of a subject for a determined preliminary scan interval. Further, a region of interest of the subject is identified The preliminary projection data is then used to perform a constrained optimization of a rapidly computable image quality metric for determining an acquisition protocol that improves the image quality metric at the identified region of interest. Particularly, the determined acquisition protocol is used to acquire target projection data corresponding to at least the identified region of interest. Further, an image of at least the identified region of interest is reconstructed using the target projection data and/or the preliminary projection data.

Certain other aspects of the present technique correspond to non-transitory computer readable media and nuclear medicine imaging systems used to implement the present method as described herein.

DRAWINGS

These and other features and aspects of embodiments of the present technique will become better understood when the following detailed description is read with reference to the accompanying drawings in which like characters represent like parts throughout the drawings, wherein.

DETAILED DESCRIPTION

The following description presents exemplary systems and methods for adaptively configuring one or more parameters associated with an imaging system for substantially improving the image quality metrics of reconstructed images of a subject. Particularly, embodiments illustrated hereinafter disclose imaging systems and methods that aim to optimize imaging parameters for acquiring sufficient projection data for enhanced image reconstruction of a targeted region of interest (ROI).

Although exemplary embodiments of the present technique are described in the context of a SPECT system, it will be appreciated that use of the present technique in various other imaging applications and systems is also contemplated. Some of these systems may include computed tomography systems, PET scanners, single or multiple detector imaging systems, X-ray tomosynthesis devices, microscopes, digital cameras and/or charge-coupled devices that acquire projection data from multiple view angles. Further, in addition to medical imaging, the techniques and configurations discussed herein can be used in pharmacological and pre-clinical research for the development and evaluation of innovative tracer compounds. By way of example, SPECT systems with rotating detectors may employ the present technique for imaging a lesion or a small region of the subject such as heart or pancreas. An exemplary environment that is suitable for practicing various implementations of the present technique is discussed in the following sections with reference to FIGS. 1-2.

Figure 1:
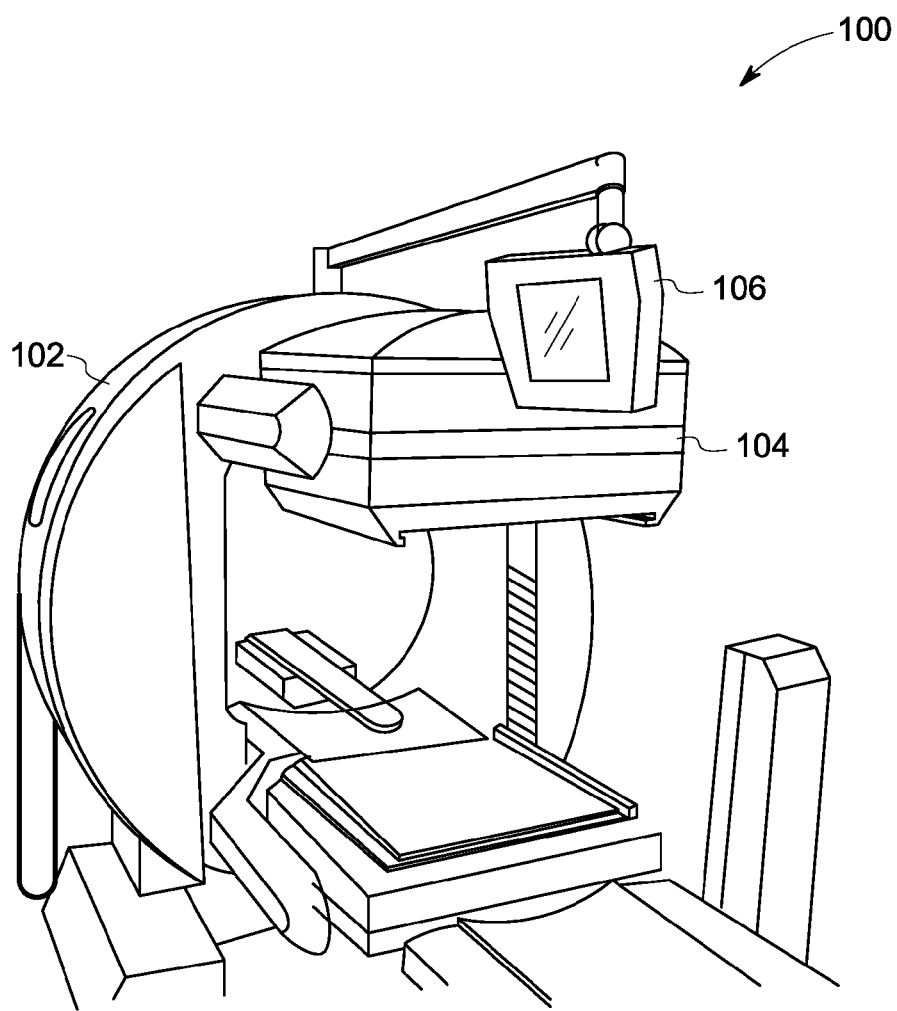
FIG. 1 is a pictorial view of an exemplary imaging system for generating images of a target object having improved image quality metrics.

FIG. 1 illustrates an exemplary adaptive imaging system 100 for acquiring and processing projection data. In one embodiment, the imaging system 100 corresponds to a SPECT system. In alternative embodiments, however, the system 100 may include other imaging modalities such a PET system or a hybrid imaging system. The hybrid imaging system, for example, includes a PET/CT or SPECT/CT scanner operable to provide emission and transmission data corresponding to PET, CT and/or SPECT images.

In one embodiment, a patient (not shown) is administered a radioisotope and placed within a SPECT scanner 102. Further, one or more detectors 104 operatively coupled to the scanner 102 are incrementally rotated about the long axis of the patient, acquiring projection data at each of a number of angular positions or "views" with respect to the patient's body. Particularly, the detectors 104 acquire projection data through interaction with gamma photons emanating from the patient. The resulting projection data from each view is communicated to a computer 106 communicatively coupled to the system 100. The computer 106 processes the projection data to obtain image reconstruction data, which in turn, is used for reconstructing two or three-dimensional images of the distribution of the radioisotope within the patient. The reconstructed images are indicative of the internal organs and/or biological functions, such as blood flow, of the patient.

As previously noted, conventional SPECT scanners that employ either a uniform scan speed or uniform scan counts for different projection views, often resulting in insufficient data acquisition. The computer 106, however, substantially optimizes a rapidly computable theoretical image quality metric over scan durations at each projection view to acquire desired values of effective count rates at different view angles. Furthermore, in certain embodiments, the computer 106 employs preliminary scan data for the optimization, thus allowing the system 100 to improve imaging performance around regions of interest. Certain exemplary components of an adaptive imaging system used in implementing the present technique will be described in greater detail with reference to FIG. 2.

Figure 2:
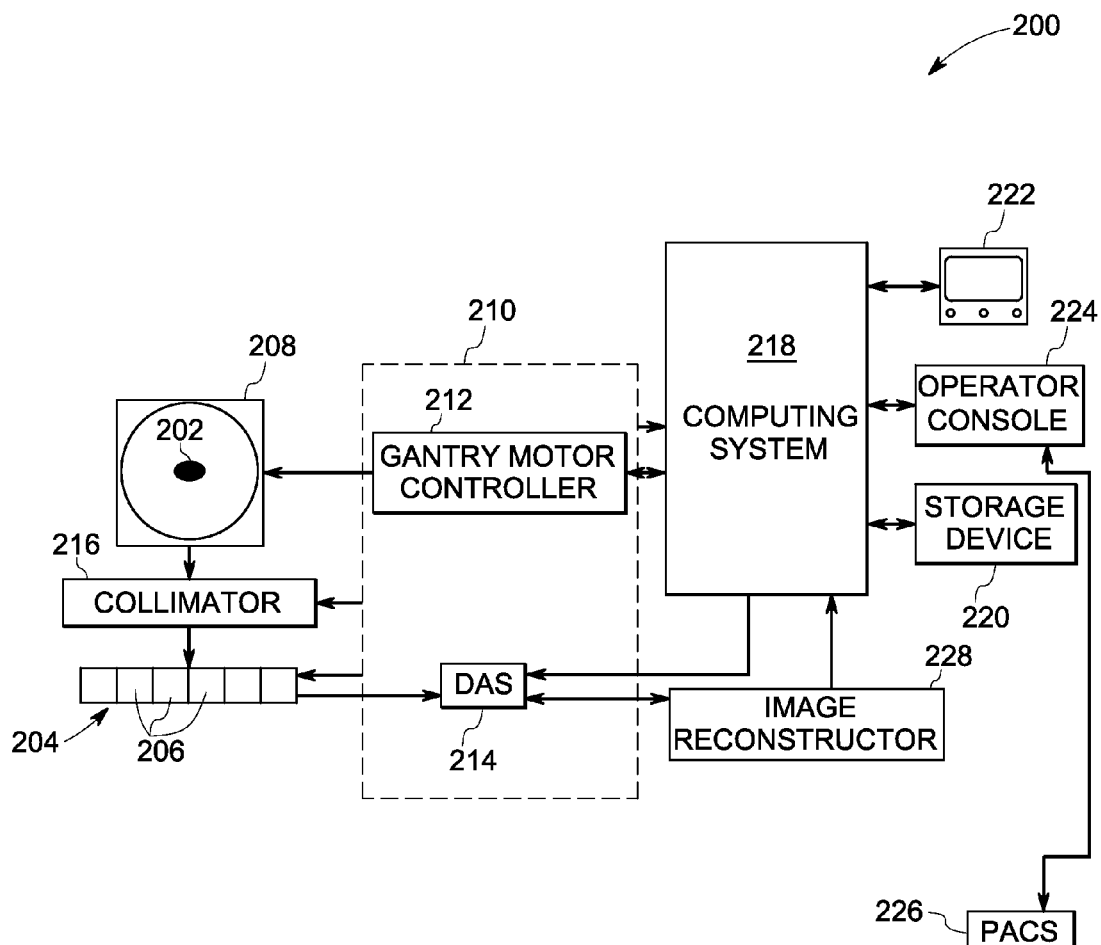
FIG. 2 is a diagrammatic illustration of exemplary components of an exemplary adaptive imaging system, in accordance with aspects of the present technique.

FIG. 2 illustrates another embodiment of an exemplary adaptive tomographic imaging system 200, similar to the system 100 illustrated in FIG. 1. Particularly, FIG. 2 illustrates certain exemplary components of the system 200 for use in implementing the present technique for improving quality metrics of a reconstructed image. Accordingly, in one embodiment, the system 200 performs a preliminary scan of a subject 202, such as a medical patient for a preliminary scan interval. Particularly, one or more parameters of the system 200 are configured to acquire sufficient data for identifying one or more ROIs of the subject 202. The system 200, for example, configures a length of the preliminary scan interval for acquiring sufficient projection data from one or more projections views. The system 200 then uses the preliminary scan data to determine certain parameters used in subsequent computations for substantially improving a metric, such as the signal-to-noise ratio (SNR) associated with the reconstructed images.

Accordingly, in one embodiment, the subject 202 is administered one or more radiopharmaceuticals or radioisotopes such as iodine-123, technetium-99m, xenon-133, thallium-201, and fluorine-18 prior to the preliminary scan. In certain embodiments, the radiopharmaceutical is combined with a specific radioligand that allows the combination to bind to a designated tissue of interest in the subject's body. Further, one or more radiation events emanating from the subject 202 owing to the activity of the radiopharmaceuticals within the subject's body are detected using a detector 204, for example, mounted on a gantry 208 in the system 200.

In particular, the detector 204 detects the radiation events emanating from the subject 202 for acquiring projection or coincidence data from multiple view angles. Accordingly, in one example, the detector 204 includes a plurality of detector elements 206 that together sense the radiation emanating from the subject 202. Further, in certain embodiments, the detector 204 is fabricated in a multi-slice configuration that includes a plurality of rows of cells or the detector elements 206 arranged in a parallel configuration for acquiring projection data. The detector elements 206, for example, include scintillators and light sensitive elements such as photomultiplier tubes and photodiodes for detecting the gamma radiation. Alternatively, the detector elements 206 include cadmium zinc telluride (CZT) based converters for direct conversion of detected radiation into electrical energy.

Generally, the detector elements 206 acquire electrical signals corresponding to emitted radiation at a variety of angular positions around the subject 202 for collecting a plurality of projection views for image reconstruction. In one embodiment, the present technique allows for rapidly optimizing one or more imaging parameters during data acquisition, such as, a distance of the detector 204 to the subject 202 in each view for efficiently imaging the ROI. Accordingly, during a scan to acquire the projection data, the system 200 configures the gantry 208 and the components mounted thereon to rotate around a rotation axis (a Z-axis) substantially coinciding with an axis of the subject 202 under examination. However, in certain embodiments where a projection angle relative to the imaged subject 202 varies as a function of time, the system 200 configures the mounted components to move along a general curve rather than along a segment of a circle.

Accordingly, the system 200 includes a control subsystem 210 that controls the rotation of the gantry 208 and the position of the detector 204 to acquire projection data from a desired view angle for a desired scan interval. To that end, the control subsystem 210, for example, includes a gantry motor controller 212 that controls the rotational speed and position of the gantry 208 based on scanning requirements. The control subsystem 210, in one embodiment, further includes a data acquisition system (DAS) 214 for sampling analog data from the detector elements 206 and converting the analog data to digital signals for subsequent processing. Particularly, the DAS 214 converts the analog signals into a digital signal, for example, indicative of the energy (z) and the location (x, y) of the corresponding event on the face of the detector 204.

Alternatively, the system 200 employs a scatter grid and/or a collimator 216 to control the direction and angular spread from which each of the detector elements 206 receive radiation. The collimator 216, in one embodiment, limits the reception of radiation along known rays. As previously noted, the DAS 214 samples and digitizes the received radiation, and transmits the digitized data, for example, to a computing system 218. The computing system 218 stores this data in a storage device 220, such as a hard disk drive, a floppy disk drive, a compact disk-read/write (CD-R/W) drive, a Digital Versatile Disc (DVD) drive, a flash drive, or a solid state storage device.

In certain embodiments, the computing system 218 includes modules and/or applications that allow for automated analysis of the preliminary scan data for identifying a target ROI, such as a lesion, and one or more parameters for use in improving quality metrics associated with the reconstructed images. In certain embodiments, the computing system 218 uses operator input in addition to the preliminary scan data for identifying the target ROI. To that end, in one embodiment, the computing system 218 is coupled to a display 222 that allows an operator to observe scanned images and/or the preliminary scan data, and indicate the target ROI, for example, using an graphical user interface (GUI). The operator can also specify commands and scanning parameters via an operator console 224 that includes a keyboard (not shown).

Although FIG. 2 illustrates only one operator console 224, more than one operator workstations can be coupled to the system 200, for example, for inputting or outputting system parameters, requesting examinations and/or viewing images. Further, in certain embodiments, the system 200 is coupled to multiple displays, printers, workstations, and/or similar devices located either locally or remotely, for example, within an institution or hospital, or in an entirely different location via one or more configurable wired and/or wireless networks such as the Internet and virtual private networks.

In one embodiment, for example, the operator console 224 includes, or is coupled to, a picture archiving and communications system (PACS) 226. Particularly, in one exemplary implementation, the PACS 226 is further coupled to a remote system (not shown), radiology department information system (RIS), hospital information system (HIS) and/or to an internal or external network (not shown) to allow operators at different locations to supply commands and parameters and/or gain access to the image data.

The computing system 218, thus, uses the preliminary scan data along with any operator-supplied data for determining system parameters for generating high quality images of the identified ROI such as a lesion without requiring explicit knowledge of the object in that region of interest. By way of example, the computing system 218 processes the preliminary scan data using a Fisher Information Matrix (FIM) for estimating contrast and variance of the lesion. Particularly, the computing system 218 employs the FIM to pre-compute and store the contributions of each projection view for a nominal scan interval, for example a one second, to an image quality metric such as a local SNR.

Additionally, the computing system 218 solves a constrained optimization problem over different scan durations to optimize the local SNR. To that end, the computing system 218 determines contributions for other scan durations using the pre-computed contributions from each view for the nominal scan. Particularly, the computing system 218 rapidly computes optimized parameter values that maximize contrast and minimize noise in the reconstructed images using the pre-computed contributions. The computing system 218 then configures one or more components of the system 200 such as the gantry 208, the detector 204 and the collimator using the values of the optimized parameters to scan and acquire projection data for generating high quality images of the target ROI.

To that end, the computing system 218 communicates the targeted scan data to an image reconstructor 228. The image reconstructor 228 uses the targeted scan data along with the preliminary scan data for reconstructing a volumetric image representation of the target ROI. In one embodiment, the reconstructor 228 either stores the generated images into the storage devices 220 and/or transmits the generated images to the display 222 or the computing system 218. The computing system 218 processes slices, projections, three-dimensional (3D) renderings and/or other image information received from the storage device 220 or the image reconstructor 228 for appropriately formatting the image representation for display and diagnosis.

Embodiments of the present technique, thus, substantially optimize a rapidly computable theoretical image quality metric over the scan durations at each projection view. The optimization aids in determining appropriate values of one or more imaging parameters such as optimal scan duration for each view, total scan duration, a view angle, collimator type and/or collimator settings for efficient imaging. Furthermore, embodiments of the present technique employ the preliminary scan data for reconstructing the final image, thus utilizing data collected at every step of the imaging process. Certain exemplary methods for improving image quality by substantially optimizing a rapidly computable theoretical metric using the present technique will be described in greater detail with reference to FIGS. 3-8.

Figure 3:
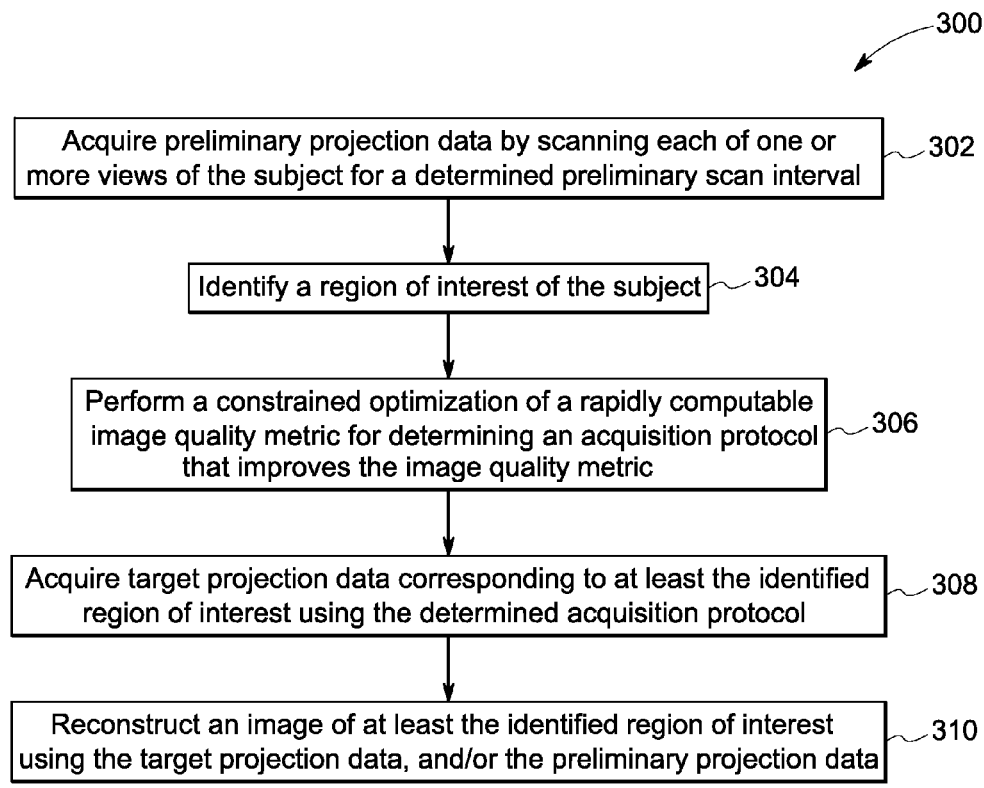
FIG. 3 is a flowchart depicting an exemplary method for generating images of a target object having a high contrast-to-noise ratio, in accordance with aspects of the present technique.

FIG. 3 illustrates a flow chart 300 depicting an exemplary method for generating images of a target object with improved image quality metrics using adaptive imaging. The exemplary method may be described in a general context of computer executable instructions stored and/or executed on a computing system or a processor. Generally, computer executable instructions may include routines, programs, objects, components, data structures, procedures, modules, functions, and the like that perform particular functions or implement particular abstract data types. The exemplary method may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 3, the exemplary method is illustrated as a collection of blocks in a logical flow chart, which represents operations that may be implemented in hardware, software, or combinations thereof. The various operations are depicted in the blocks to illustrate the functions that are performed, for example, during data acquisition, processing and image reconstruction phases of the exemplary method. In the context of software, the blocks represent computer instructions that, when executed by one or more processing subsystems, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of FIGS. 1-2.

Generally, tomographic imaging such as SPECT imaging is used to generate two or 3D images for various diagnostic and/or prognostic purposes. Conventional imaging techniques allow for a tradeoff between various imaging criteria such as image quality, spatial resolution, noise, radiation dose, system size and associated costs. Certain clinical applications, however, entail use of images in high spatial resolution for investigating minute features within a subject, such as in an around a human heart. Particularly, accurate characterization of specific features corresponding to the thoracic cavity allows for a better understanding of the physiology of heart and lungs, which in turn, aids in early detection of various cardiovascular and lung diseases.

A conventional SPECT system, however, employs either a uniform scan speed or uniform scan counts, which determines the time that a detector remains at a specific view angle for acquiring "counts" or gamma absorption events. The acquired data quality, thus, often varies significantly from one view angle to another, for example, owing to the ROI characteristics, attenuation and finite collimator resolution resulting in different effective count rates at different view angles. In a SPECT implementation using a uniform scan, the time spent by the detector at each angle, thus, may be either longer or shorter than appropriate to gather sufficient projection data for generating the image of a desired spatial resolution.

Accordingly, embodiments of the present method describe an adaptive imaging technique for determining appropriate values of an imaging parameter for different projection views that optimize image quality metrics associated with a reconstructed image. For discussion purposes, an embodiment of the present method will be described with reference to an adaptive per-view scan interval allocation technique for improving quantitation by maximizing the contrast-to-noise ratio (CNR) at a given ROI. However, it may be noted, that the embodiments of present method is also applicable to configure other imaging parameters such as different collimators types, dimensions and/or detectors used at each view. In such implementations, the present method optimizes the collimator and detector parameters in addition to or instead of the scan intervals.

At step 302, an imaging system such as the system 100, 200 of FIGS. 1-2 acquires preliminary projection data from one or more views of a subject. To that end, the system 200 scans each of the one or more views for a preliminary scan interval using a preliminary scan or a scout scan. Particularly, the system 200 configures a length of the preliminary scan interval in relation to a total scan interval for acquiring sufficient projection data for achieving a desired tradeoff between two or more image quality metrics based on one or more imaging requirements. In one embodiment, for example, the system 200 performs a preliminary scan for about 10 or 20 percent of the total scan interval for acquiring sufficient imaging data for subsequent analysis and image reconstruction. The scout scan, thus allows generation of a good quality image while the remaining scan interval can then be used for improving imaging performance around the target ROI during the targeted scan.

Further, at step 304, the system 200 identifies a target ROI of the subject 202. In one embodiment, system 200 identifies the ROI without explicit knowledge of the anomaly such as a lesion or nodule in that ROI. To that end, the system 200 displays the preliminary projection data and/or one or more corresponding images on the display 222 for evaluation by an operator. The operator analyzes the preliminary projection data and/or corresponding images to identify the target ROI from the acquired preliminary projection data. Specifically, in one example, the operator reviews the preliminary projection data indicative of regions of increased activity concentration as compared to surrounding tissues to identify the target ROI using a GUI.

Alternatively, the system 200 employs any previously available medical information, such as a previously performed computed tomography (CT) scan data to identify the approximate position of the target ROI. In certain embodiments, the system 200 employs computer aided evaluation, automated tools and/or applications for identifying the target ROI. The automated tools, for example, use one or more techniques such as segmentation or identifying specific signatures of the structures using matched filters or Eigen analysis for identifying the target ROI. In certain embodiments, the target ROI is identified based on any structural anomalies such as lesions or nodules detected during previous examinations.

As previously noted, the system 200 also uses the preliminary projection data for computing parameters for use in subsequent optimizations. Accordingly, at step 306, the system performs a constrained optimization of a rapidly computable image quality metric using the preliminary projection data. In one embodiment, the image quality metric, for example, includes the SNR or the CNR at the identified ROI. Particularly, the system 200 performs the constrained SNR or CNR optimization for determining an acquisition protocol that improves the SNR or CNR metric at the identified region of interest. In one implementation, for example, the system 200 employs a rapidly computable theoretical CNR expression for penalized likelihood estimators with quadratic penalties. The CNR metric and constraints are designed to discard heavily asymmetrical scan time allocations that produce very low contrast. Further, in one embodiment, the system 200 imposes smoothness constraints on the adapted imaging parameters for enhanced imaging. By way of example, the system 200 imposes smoothness constraints that configure imaging parameters to discourage large changes in view-to-view scan times for optimized imaging of the ROI.

To that end, in one embodiment, the system 200 generates a FIM using the preliminary projection data. Typically, the FIM is used to calculate the covariance matrices associated with maximum-likelihood estimates. The FIM, for example, may be represented using equation 1 presented herein.

$$F(s) \equiv P(s)^T diag\left\{\frac{1}{\bar{y}_i(s)}\right\} P(s) \quad \text{(Equation 1)}$$

In Equation 1, "F" corresponds to the Fisher Information Matrix, "P" corresponds to a system matrix, "T" denotes the transpose operator, "$\bar{y}_i$" corresponds to mean counts at detector "i," and "s" corresponds to a vector of scan times at each view.

Particularly, the system 200 processes the preliminary projection data to estimate mean values employed by the FIM for rapidly estimating a contrast metric and/or a noise metric for the identified ROI or lesion. By way of example, the system 200 uses the linearized local impulse response (LLIR) depicted in equation 2 presented herein for estimating the contrast metric.

$$LLIR_j^{j'}(s) \approx q_{j'}^t diag\left\{\frac{f_i^j(s)}{f_i^j(s) + \beta\mu_i}\right\} q_j \quad \text{(Equation 2)}$$

In Equation 2, the term "q" refers to a column of the Discrete Fourier Transform (DFT) matrix, "f" corresponds to the DFTs of the centered columns of the FIM, "μ" corresponds to the second derivative matrix of the quadratic penalty, while β denotes the strength of the quadratic penalty.

The noise metric, for example, may be represented using the voxelwise standard deviation depicted in equation 3 presented herein.

$$var_j(s) \approx q_{j'}^T diag\left\{\frac{f_i^j(s)}{(f_i^j(s) + \beta\mu_i)^2}\right\} q_j \quad \text{(Equation 3)}$$

The system 200 then uses the estimated contrast and noise metrics for determining the acquisition protocol that maximizes the image quality metric at the identified ROI. Use of the estimated contrast and noise metric, thus, allows rapid computability of the image quality metric for generating a good quality image, while still improving imaging performance around the ROI.

To that end, in one embodiment, the system 200 pre-computes a nominal contribution of an imaging parameter to the image quality metric for each view scanned for a nominal scan interval. By way of example, the system 200 pre-computes the contribution of each view to the local CNR when scanned, for example, for one second. The system 200 iteratively adapts a value of the imaging parameter for each view until the adapted value allows the system 200 to achieve a designated improvement in the image quality metric. To that end, the system 200 quickly scales the pre-computed nominal contributions for each view to compute the contributions of each view for a candidate scanning protocol. Use of the pre-computed contributions prevents the need to calculate each of the candidate protocol contributions individually, thus allowing faster computation.

Additionally, as the nominal contributions have been pre-computed, the system 200 rapidly computes optimal values for an imaging protocol that maximizes or at least substantially improves the image quality metric over the total scan interval. In one embodiment, for example, the system 200 iteratively adapts scan intervals for the different views by combining the corresponding contrast and noise metrics. Particularly, the system 200 determines an appropriate scan interval allocation such that subsequent target projection data acquisition from the different views using the determined scan intervals minimizes the noise or variance while maximizing the contrast at the identified ROI. In one embodiment, for example, the system estimates the CNR metric by dividing the LLIR by the voxelwise variance.

An exemplary CNR metric, for example, may be represented using the equation 4 presented herein.

$$CNR_j(\underline{s}) \equiv \frac{LLIR_j^j(\underline{s}) - \max_{j' \in N_j} LLIR_j^{j'}(\underline{s})}{std_j(\underline{s})} \quad \text{(Equation 4)}$$

In Equation 4, the term $N_j$ corresponds to the neighborhood of voxel j, over which the LLIR is computed. Furthermore, in certain embodiments, the system 200 determines the appropriate scan intervals for each of the views by optimizing the CNR metric under one or more constraints. These constraints, for example, entail that the determined scan interval for each view is at least equal to the preliminary scan interval, the determined scan interval for each view is less than a designated maximum interval, and/or the total scan interval remains constant. An exemplary representation of the determined scan intervals may be represented using the equation 5 presented herein.

$$\underline{s}^* = \underset{\underline{s} \in S \equiv \{\underline{s} | t_{max} \geq s_v \geq t_{scout}\}}{\operatorname{argmax}} CNR_j(\underline{s}) \quad \text{(Equation 5)}$$

In Equation 5, the term $t_{max}$ corresponds to the vector of maximum allowable scan times at each view and $t_{scout}$ to vector of scout scan durations t Such adaptive optimization of image quality metrics, such as the CNR, using the determined acquisition protocol allows control of the scanning interval, collimation, geometry and radiation dose. Additionally, the adaptive optimization greatly improves the imaging performance in the neighborhood of the ROI. In certain embodiments, the system 200 employs the determined acquisition protocol for iteratively adapting one or more other imaging parameters such as type, size, configuration and/or position of the collimator or detector for each view. Particularly, one or more of these parameters are iteratively adapted until the adapted value of the imaging parameter achieves a designated improvement in the SNR or CNR metric.

Further, at step 308, the system 200 acquires target projection data corresponding to at least the identified ROI using the determined acquisition protocol. The system 200 then communicates the targeted scan data to the image reconstructor 228. At step 310, the image reconstructor 228 uses the targeted scan data to reconstruct one or more images of the target ROI. In certain embodiments, the image reconstructor 228 uses preliminary scan data and any information relating to the scanned subject 202 acquired before the targeted scan or input by the user in addition to the targeted scan data for reconstructing an image of the target ROI.

Particularly, in one embodiment, the preliminary scan data finds use in establishing the subject size, shape and activity distribution. Accordingly, the image reconstructor 228 employs the preliminary scan data along with the targeted scan data for image reconstruction. Alternatively, the image reconstructor 228 uses sinogram data generated using the preliminary scan to supplement the sinogram data generated from the targeted scan of the target ROI for image reconstruction. Use of the additional sinogram data, thus, allows for reconstructing images including one or more features of the target ROI with maximal image quality as defined by the chosen image quality metric. In certain embodiments, the image reconstructor 228 transmits the images to the computing system 218 and/or the display 222. Subsequently, the computing system 218 and/or an operator may analyze the reconstructed images of the target ROI for diagnosing a pathological state of the imaged tissues of the subject 202.

Constrained optimization of a rapidly computable image quality metrics, thus, allows determining an acquisition protocol that maximizes the image quality metric at the ROI without requiring additional scanning time or radiation dose compared to conventional non-adaptive scans. The optimization is performed under the constraints that the total scan interval is fixed and that the scan interval at each view is at least equal to the time spent at that view during the preliminary scan. Accordingly, the present method avoids wastage of preliminary scan data by using the preliminary scan data as part of the final dataset for generating high quality reconstructions of the target ROI useful in diagnosing a health condition of the subject.

Figure 4:
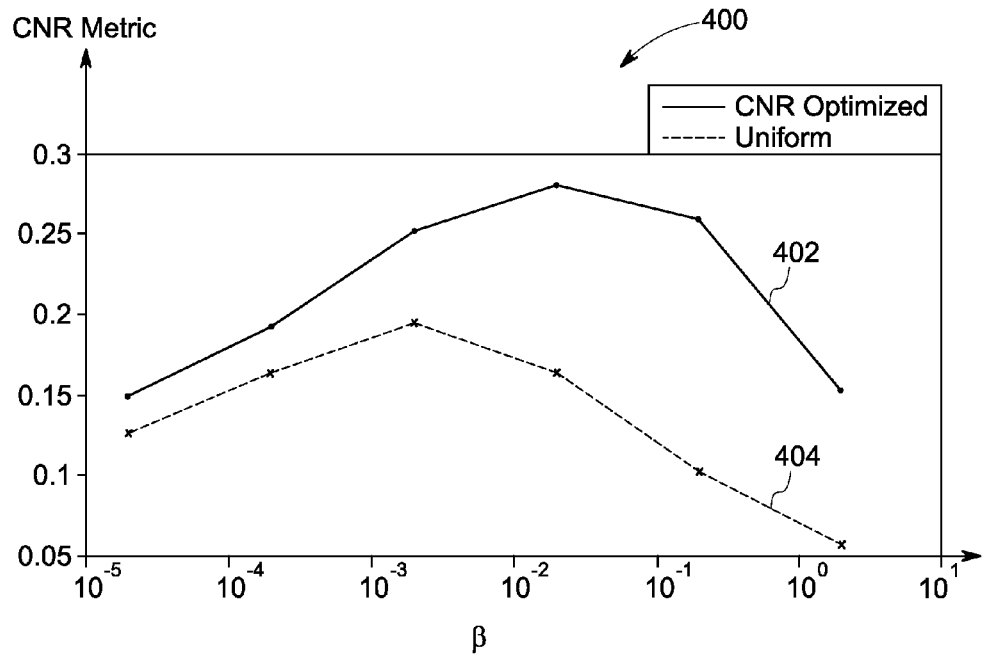
FIGS. 4-6 illustrate results of an exemplary simulation performed using the exemplary method described with reference to FIG. 3.
Figure 5:
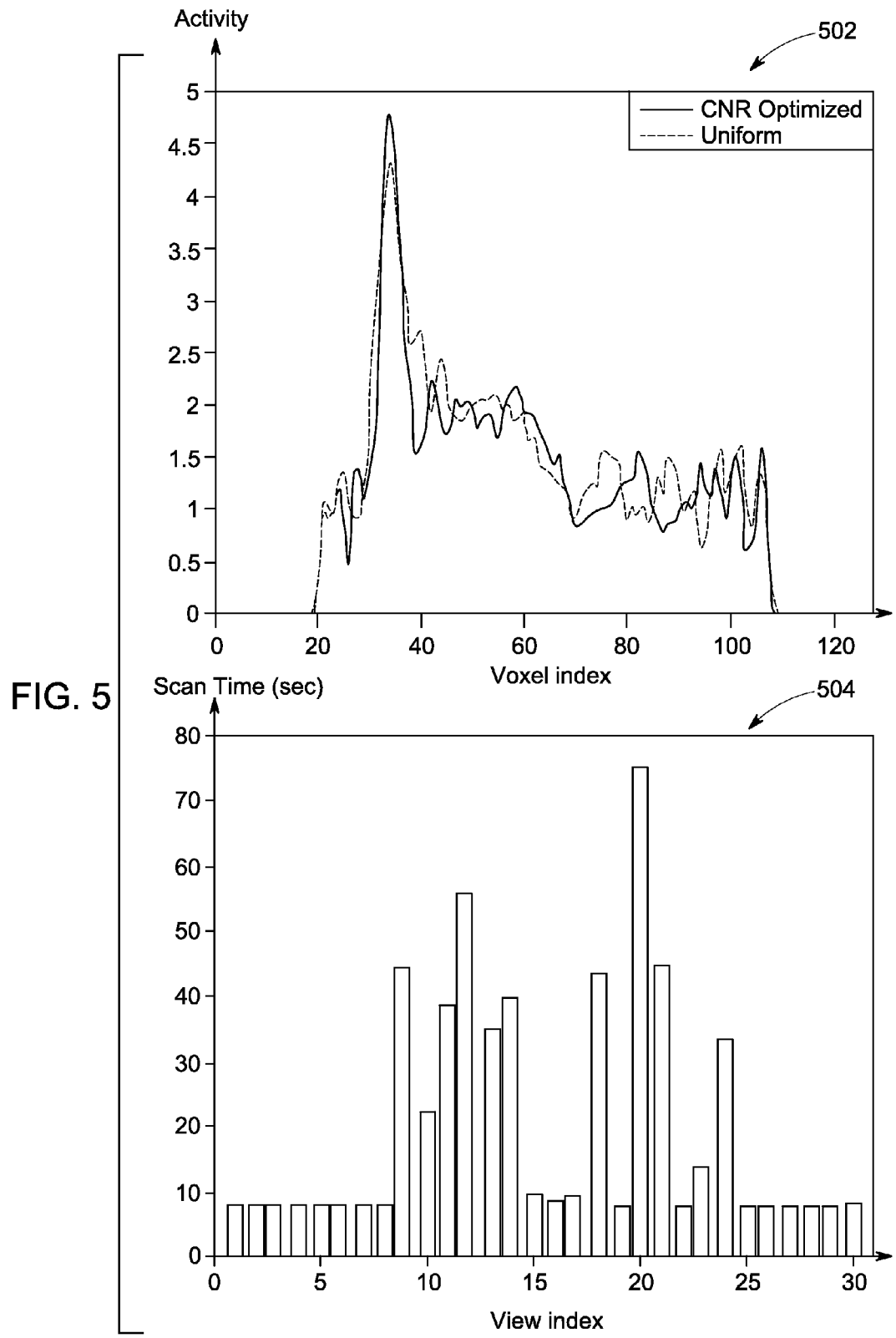
Figure 6:
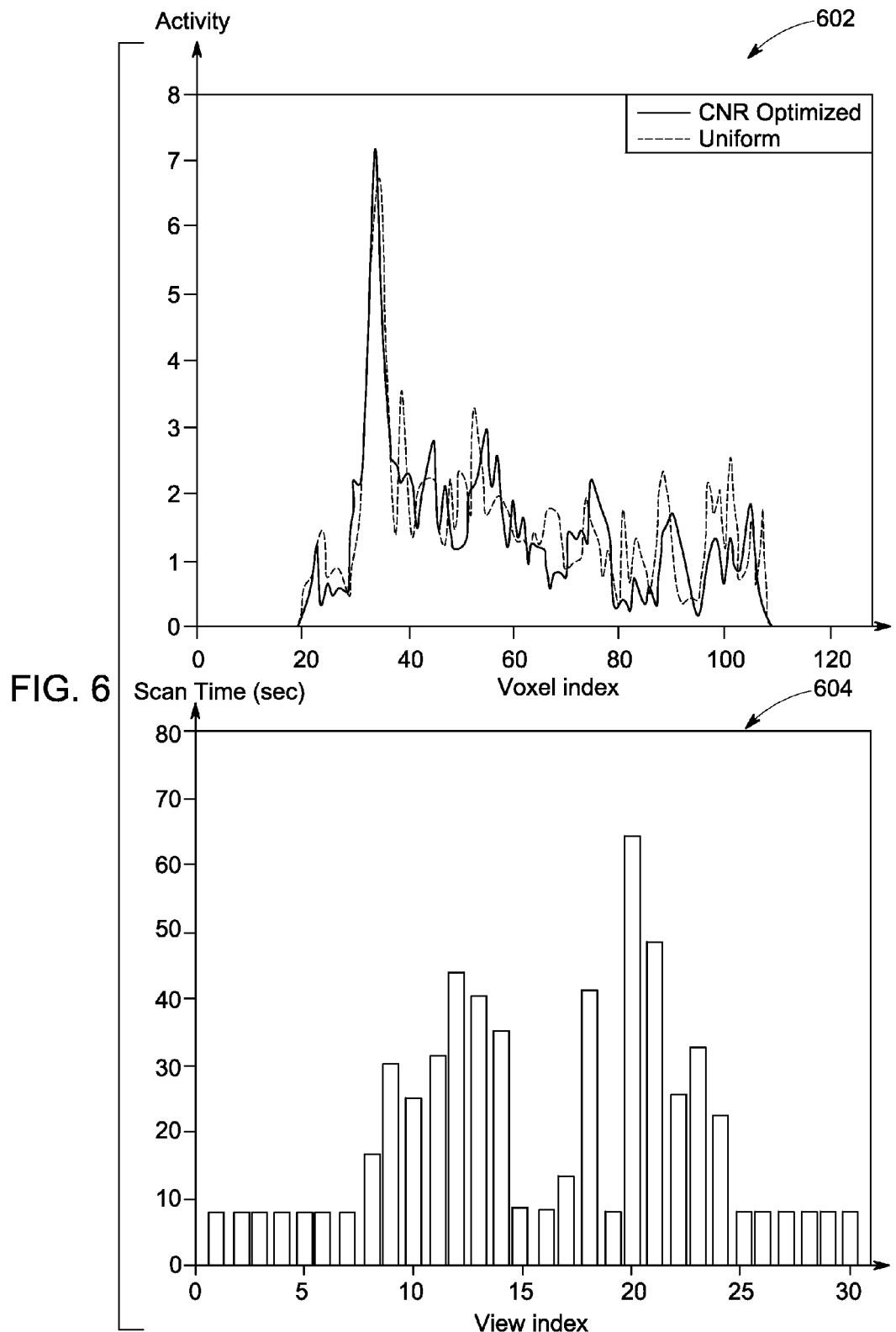

Further, FIGS. 4-6 illustrate results of an exemplary simulation performed using the exemplary method described with reference to FIG. 3. In particular, FIGS. 4-6 illustrate results of a simulation of an anthropomorphic phantom. For the simulation, 4-to-1 contrast lesions of various sizes were inserted into the phantom and the ROI was a 15 mm lesion centered at a location inside the liver. Projection data dimensions were 128 (radial) ×64 (axial) with 30 views. Further, 4 mm x 35 mm parallel hole collimators with 4 mm×4 mm detectors were used. Additionally, geometry and depth-dependent attenuation were modeled. The total scan time was fixed at 10 minutes and mean counts per scan was 4.5 Million (M). Twenty Monte Carlo (MC) noise realizations were generated. Further, a corresponding scout scan was set to 40% of the total scan duration at 8 seconds/view for a total of 4 minutes.

Particularly, FIG. 4 illustrates a graphical representation 400 depicting optimized CNR values over a range of smoothing parameters, β. The graphical representation 400 further compares the optimized CNR values 402 achieved using the method of FIG. 3 with CNR values 404 achieved using uniform scans. In particular, the graphical representation 400 indicates β=0.02 as the optimal smoothing level, further indicating improvements over the uniform scan over all smoothing levels.

FIGS. 5 and 6 illustrate lesion profiles 502, 602 and CNR optimized scan times 504, 604 for CNR-optimized and uniform scans for a near-optimal smoothing parameter, for example, β=0.002 (about 30% predicted improvement) and an optimal smoothing parameter, for example, β=0.02 (about 72% predicted improvement). Contrast recovery for the lesion was calculated using mean activities at all lesion voxels and a background region just outside the lesion. The standard deviations were calculated as the mean voxelwise standard deviations at all lesion voxels. As the CNR optimization was performed using only the voxel at the center of the lesion, the applicability of single-voxel-based optimization on a slightly larger ROI was also investigated.

As illustrated by FIGS. 5 and 6, the CNR-optimized scan time allocations 504, 604 improved the lesion CNR for both smoothing levels by substantially preserving contrast and significantly reducing the standard deviation. For β=0.02, contrast improved by 11% and noise reduced by 34%. For β=0.002, contrast was slightly lower by 2% but noise was reduced by 37%. In both cases, the CNR improved by more than 50% over uniform scans but the noise textures around the lesion were also different for the CNR optimized scans. It may be noted that the heavily weighted views were highly sensitive to the lesion, while the other views, especially orthogonal views, were weighted sufficiently to preserve contrast.

Embodiments of the present methods and systems, thus, disclose an efficient technique for adaptive imaging. Particularly, embodiments described herein allow for constrained optimization of rapidly computable image quality metrics, which in turn, allows determining an acquisition protocol that maximizes the image quality metrics at the ROI. Additionally, the described embodiments allow rapid computability of the image quality metrics for generating a good quality image, while still improving performance around the ROI. Furthermore, as the optimization is performed under specific constraints the present method prevents wastage of preliminary scan data. Specifically, preliminary scan data is used as part of the final dataset for generating high quality reconstructions of the target ROI useful in diagnosing a health condition of the subject without requiring additional scanning time or radiation dose.

Furthermore, the foregoing examples, demonstrations, and process steps, for example, those that may be performed by the control subsystem 210, the gantry motor controller 212, the DAS 214, the computing system 218 and the image reconstructor 228 may be implemented by suitable code on a processor-based system. Additionally, it may be noted that one or more of certain components illustrated in in FIGS. 1-2, such as those listed herein may be combined into one or more devices for performing corresponding functions.

It should also be noted that different implementations of the present technique may perform some or all of the steps described herein in different orders or substantially concurrently, that is, in parallel. In addition, the functions may be implemented in a variety of programming languages, including but not limited to Python, C++ or Java. Such code may be stored or adapted for storage on one or more tangible, machine-readable media, such as on data repository chips, local or remote hard disks, optical disks (that is, CDs or DVDs), solid-state drives or other media, which may be accessed by a processor-based system to execute the stored code.

While only certain features of the present invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for adaptive imaging, comprising:
acquiring preliminary projection data by scanning each of one or more views of a subject for a determined preliminary scan interval;
identifying a region of interest of the subject;
performing a constrained optimization of a rapidly computable image quality metric using the preliminary projection data for determining an acquisition protocol that improves the image quality metric at the identified region of interest, wherein performing the constrained optimization comprises:
estimating one or more of a contrast metric and a noise metric associated with the identified region of interest using the preliminary projection data; and
combining the contrast metric and the noise metric for determining the acquisition protocol;
acquiring target projection data corresponding to at least the identified region of interest using the determined acquisition protocol; and
reconstructing an image of at least the identified region of interest using the target projection data, the preliminary projection data, or a combination thereof.

2. The method of claim 1, further comprising determining the preliminary scan interval out of a total scan interval for achieving a desired tradeoff between two or more image quality metrics based on one or more imaging requirements.

3. The method of claim 1, comprising reconstructing an image of the subject using the preliminary projection data for identifying the region of interest.

4. The method of claim 1, wherein identifying the target region of interest comprises evaluating the preliminary projection data using operator input, automated tools, computer aided analysis, prior examination data, or combinations thereof.

5. The method of claim 1, comprising identifying the region of interest using the subject's previously available medical information.

6. The method of claim 1, wherein performing a constrained optimization of the rapidly computable image quality metric comprises:
generating a fisher information matrix using the preliminary projection data;
estimating one or more of the contrast metric and the noise metric associated with the identified region of interest using the fisher information matrix; and
combining the contrast metric and the noise metric for determining the acquisition protocol that maximizes the image quality metric at the identified region of interest.

7. The method of claim 1, wherein the image quality metric comprises signal-to-noise ratio, contrast-to-noise ratio, or a combination of signal energy, signal contrast and image noise.

8. The method of claim 1, wherein determining the acquisition protocol comprises determining appropriate scan intervals for each of the one or more views such that acquiring projection data from each of the one or more views using the determined scan intervals maximizes the image quality metric at the identified region of interest.

9. The method of claim 1, wherein performing the constrained optimization comprises determining appropriate scan intervals for each of the one or more views such that a total scan interval for scanning the subject is fixed, and wherein each of the scan intervals determined for each of the one or more views is at least equal to the preliminary scan interval.

10. The method of claim 9, wherein performing the constrained optimization comprises imposing a smoothness constraint on the scan intervals to discourage large changes in view-to-view scan times.

11. The method of claim 1, wherein performing the constrained optimization comprises determining an appropriate collimator type, a collimator size, a collimator configuration, an detetcor type, a detector size, a detector position, a detector configuration, or combinations thereof, that improve the image quality metric at the identified region of interest.

12. The method of claim 11, wherein performing the constrained optimization comprises imposing a smoothness constraint on collimator parameters, detector parameters, or a combination thereof to discourage large changes in their values between subsequent views.

13. The method of claim 1, wherein performing the constrained optimization comprises:
computing a nominal contribution of an imaging parameter to the image quality metric in each of the one or more views, wherein the one or more views are scanned for a nominal scan time; and
iteratively adapting a value of the imaging parameter for each view in the one or more views based on the nominal contribution computed for the view until the adapted value of the imaging parameter achieves a designated improvement in the image quality metric.

14. The method of claim 13, wherein the imaging parameter comprises one or more of a corresponding scan interval, a collimator type, a collimator size, a collimator configuration, an detector type, a detector size, a detector position, a detector configuration, or combinations thereof, for each of the one or more views.

15. A non-transitory computer readable medium that stores instructions executable by one or more processors to perform a method for adaptive imaging, comprising:
acquiring preliminary projection data by scanning each of one or more views of a subject for a determined preliminary scan interval;
identifying a region of interest of the subject;
performing a constrained optimization of a rapidly computable image quality metric using the preliminary projection data for determining an acquisition protocol that improves the image quality metric at the identified region of interest, wherein performing the constrained optimization comprises:
estimating one or more of a contrast metric and a noise metric associated with the identified region of interest using the preliminary projection data; and
combining the contrast metric and the noise metric for determining the acquisition protocol;
acquiring target projection data corresponding to at least the identified region of interest using the determined acquisition protocol; and
reconstructing an image of at least the identified region of interest using the target projection data, the preliminary projection data, or a combination thereof.

16. The non-transitory computer readable medium of claim 15, wherein performing a constrained optimization of the rapidly computable image quality metric comprises:
generating a fisher information matrix using the preliminary projection data;
estimating one or more of the contrast metric and the noise metric associated with the identified region of interest using the fisher information matrix; and
combining the contrast metric and the noise metric for determining the acquisition protocol that maximizes the image quality metric at the identified region of interest.

17. The non-transitory computer readable medium of claim 15, wherein determining the acquisition protocol comprises determining appropriate scan intervals for each of the one or more views such that acquiring projection data from each of the one or more views using the determined scan intervals maximizes the image quality metric at the identified region of interest.

18. The non-transitory computer readable medium of claim 15, wherein performing the constrained optimization comprises:
computing a nominal contribution of an imaging parameter to the image quality metric in each of the one or more views, wherein the one or more views are scanned for a nominal scan time; and
iteratively adapting a value of the imaging parameter for each view in the one or more views based on the nominal contribution computed for the view until the adapted value of the imaging parameter achieves a designated improvement in the image quality metric.

19. An nuclear imaging system, comprising:
one or more detectors configured to move about a subject to acquire projection data from one or more views; and
a controller configured to vary a scan interval for which one or more of the detectors remains at a particular view in the one or more views in response to one or more control signals;
a computing system coupled to one or more of the detector and the controller, wherein the computing system:
provides one or more of the control signals to one or more of the detectors to acquire preliminary projection data by scanning each of one or more views of the subject for a determined preliminary scan interval;
identifies a region of interest of the subject;
performs a constrained optimization of a rapidly computable image quality metric using the preliminary projection data for determining an acquisition protocol that improves the image quality metric at the identified region of interest, wherein performing the constrained optimization comprises estimating one or more of a contrast metric and a noise metric associated with the identified region of interest using the preliminary projection data and combining the contrast metric and the noise metric for determining the acquisition protocol;
provides one or more of the control signals to one or more of the detectors to acquire target projection data corresponding to at least the identified region of interest using the determined acquisition protocol; and
reconstructs an image of at least the identified region of interest using the target projection data, the preliminary projection data, or a combination thereof.

20. The nuclear medicine imaging system of claim 19, wherein the imaging system comprises a single or multiple detector imaging system, a rotating positron emission tomography (PET) scanner, a rotating single photon emission computed tomography (SPECT) scanner, a dual head coincidence imaging system, a SPECT scanner comprising variable collimators, a SPECT system comprising one or more collimators configured to move in relation to one or more detectors, or combinations thereof.

* * * * *